United States Patent
Pohl et al.

(10) Patent No.: US 7,615,662 B2
(45) Date of Patent: Nov. 10, 2009

(54) PROCESS FOR THE PREPARATION OF ISOCYANATES IN THE GAS PHASE

(75) Inventors: Fritz Pohl, Brunsbüttel (DE); Klaus Biskup, Leverkusen (DE); Rainer Bruns, Leverkusen (DE); Friedhelm Steffens, Leverkusen (DE); Herbert Stutz, Dormagen (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/001,270

(22) Filed: Dec. 11, 2007

(65) Prior Publication Data

US 2008/0167490 A1    Jul. 10, 2008

(30) Foreign Application Priority Data

Dec. 13, 2006    (DE)    ........................ 10 2006 058 634

(51) Int. Cl.
*C07C 263/00*    (2006.01)
(52) U.S. Cl. ........................................ 560/347; 560/352
(58) Field of Classification Search ................... 560/347
See application file for complete search history.

(56) References Cited

U.S. PATENT DOCUMENTS

| | | | |
|---|---|---|---|
| 4,847,408 A | 7/1989 | Frosch et al. | 560/347 |
| 5,391,683 A | 2/1995 | Joulak et al. | 528/67 |
| 5,449,818 A | 9/1995 | Biskup et al. | 560/347 |
| 5,679,839 A | 10/1997 | Armand et al. | 560/347 |
| 6,800,781 B2 | 10/2004 | Herold et al. | 560/347 |
| 7,084,297 B2 | 8/2006 | Woelfert et al. | 560/347 |
| 2004/0068137 A1 | 4/2004 | Herold et al. | 560/347 |
| 2005/0070734 A1 | 3/2005 | Wölfert et al. | 560/347 |

FOREIGN PATENT DOCUMENTS

WO    2005/123665 A1    12/2005

*Primary Examiner*—Sikari A Witherspoon
(74) *Attorney, Agent, or Firm*—Lyndanne M. Whalen; Noland J. Cheung

(57) ABSTRACT

Isocyanates are produced by reaction of primary amines with phosgene in the gas phase. In this process, the reaction is terminated by guiding the reaction mixture from the reaction chamber through a cooling stretch into which liquids are injected. Direct cooling takes place in the cooling stretch in one stage in two or more cooling zones connected in series.

11 Claims, No Drawings

PROCESS FOR THE PREPARATION OF ISOCYANATES IN THE GAS PHASE

BACKGROUND OF THE INVENTION

This invention relates to a process for the preparation of isocyanates by reaction of corresponding primary amine(s) with phosgene in the gas phase. In this process, the reaction is terminated by guiding the reaction mixture out of the reaction chamber through a cooling stretch into which liquids are injected. Direct cooling takes place in the cooling stretch in one stage in two or more cooling zones connected in series.

Various processes for the preparation of isocyanates by reaction of amines with phosgene in the gas phase are known from the prior art. The advantages of these procedures are that intermediates that are difficult to phosgenate are avoided, high reaction yields can be achieved, the phosgene hold-up is reduced, and the amount of energy specifically required for the preparation of the isocyanates is relatively small.

EP-A-593 334 describes a process for the preparation of aromatic diisocyanates in the gas phase, characterised in that the reaction of the diamine with phosgene takes place in a tubular reactor without moving parts and with a narrowing of the walls along the longitudinal axis of the tubular reactor. However, the process is problematic because mixing of the starting material streams solely via a narrowing of the tube wall is poor as compared with the use of a proper mixing member. Poor mixing conventionally leads to undesirably high solids formation.

EP-A-699 657 describes a process for the preparation of aromatic diisocyanates in the gas phase, characterised in that the reaction of the associated diamine with the phosgene takes place in a two-zone reactor, wherein the first zone, which accounts for approximately from 20% to 80% of the total reactor volume, is ideally mixed and the second zone, which accounts for from 80% to 20% of the total reactor volume, can be characterised by a piston flow. However, because at least 20% of the reaction volume is ideally back-mixed, non-uniform dwell time distribution results, which can lead to undesirably increased solids formation.

EP-A-289 840 describes the preparation of diisocyanates by gas-phase phosgenation in a turbulent flow at temperatures of from 200° C. to 600° C. in a cylindrical chamber without moving parts. Because there are no moving parts, the risk of phosgene escaping is reduced. Due to the turbulent flow in the cylindrical chamber (tube), relatively good equipartition of flow in the tube is achieved, and accordingly a relatively narrow dwell time distribution is obtained. If fluid elements in the vicinity of the wall are disregarded, this can, as described in EP-A-570 799, lead to a reduction in solids formation.

EP-A-570 799 discloses a process for the preparation of aromatic diisocyanates in which the reaction of the associated diamine with the phosgene is carried out in a tubular reactor, above the boiling point of the diamine, within a mean contact time of from 0.5 to 5 seconds. As is described in the specification, both too long and too short a reaction time lead to undesirable solids formation. A process is therefore disclosed in which the mean deviation from the mean contact time is less than 6%. The contact time is observed by carrying out the reaction with a tubular flow that is characterised by either a Reynolds number above 4000 or a Bodenstein number above 100.

As already disclosed in EP-A-570 799, a common feature of all the processes known from the prior art for the preparation of isocyanates by reaction of amines with phosgene is that the isocyanates formed are not thermally stable at the reaction temperatures of from 300 to 600° C. that are conventionally used. It is therefore necessary to effectively terminate the reaction once an optimal reaction time has been reached in order to avoid the formation of undesirable secondary products by thermal decomposition of the isocyanate or by a further reaction.

To this end, in EP-A-0 289 840, the gaseous mixture that is continuously leaving the reaction chamber and that contains inter alia isocyanate that has formed, phosgene and hydrogen chloride is introduced into an inert solvent, for example dichlorobenzene. A disadvantage of this process is that the flow speed with which the gas mixture is passed through the solvent bath must be chosen to be relatively low because, at too high a speed, solvent and the compounds dissolved therein would be carried along. The liquid compounds would have to be separated from the gas in a subsequent step. A further disadvantage is that, owing to the low flow speeds and a poor heat transfer system, large solvent containers must be used to achieve cooling.

Also known are processes which use heat exchangers for cooling the reaction gases and/or expanding the gases in vacuo (DE 101 58 160 A1). The disadvantage of heat exchangers is that, because of the poor heat transfer, large exchange surfaces and accordingly large heat exchangers are required for effective cooling. In addition, solids are deposited on the comparatively cold surfaces of the heat exchangers as a result of secondary reactions of the gas mixture on those surfaces, such as, for example, decomposition or polymerization. The heat transfer is further impaired as a result, leading to a longer dwell time and accordingly a further increase in secondary product formation. Moreover, cleaning of the cooling stage results in undesirable stoppage times for the installation as a whole.

According to the teaching of EP-A-1 403 248, the problem of rapidly cooling the gaseous reaction mixture in the gas-phase phosgenation of amines with phosgene to a temperature at which the reaction product in question is thermally stable, while avoiding the mentioned disadvantages, and at the same time suppressing the formation of undesirable secondary products can be solved by cooling the reaction mixture leaving the reaction chamber in a single cooling zone by direct cooling while injecting a cooling liquid. EP-A-1 403 248 discloses a process for quenching a gaseous reaction mixture in the phosgenation of diamines in the gas phase to prepare diisocyanates in which the gaseous reaction mixture comprises at least one diisocyanate, phosgene and hydrogen chloride, by injecting a quench liquid into the gas mixture flowing continuously from a cylindrical reaction zone into the downstream cylindrical quench zone, the quench liquid being injected by means of at least two spray nozzles arranged at the entry to the quench zone at equal intervals along the periphery of the quench zone.

According to the teaching of EP-A-1 403 248, as well as containing phosgene, hydrogen chloride and the diisocyanate formed as the principal product, the gaseous reaction mixture can include other isocyanates, which are formed as secondary products, as well as nitrogen and/or organic solvents. As diisocyanates prepared by the gas-phase phosgenation of diamines, EP-A-1 403 248 discloses hexamethylene diisocyanate (HDI), isophorone diisocyanate (IPDI), naphthylene diisocyanate (NDI), toluene diisocyanate (TDI), diphenylmethane diisocyanate, dicyclohexylmethane diisocyanate (HMDI). According to the teaching of EP-A-1 403 248, the advantage of the process is that, by the spraying of a suitable quench liquid, the desired rapid cooling of the gas mixture, which comprises a diisocyanate, hydrogen chloride and excess phosgene, as it leaves the reactor from 300 to 400° C.

to a maximum of 150° C. is achieved. The contact time, in which cooling takes place, is from 0.2 to 3 seconds.

The direct cooling of the reaction mixture, disclosed in EP-A-1 403 248, during the preparation of isocyanates by the gas-phase phosgenation of corresponding amines with phosgene is likewise the subject-matter of WO 2005/123665. The cooling times of from 0.2 to 3 seconds disclosed in EP-A-1 403 248 lead, according to the teaching of WO 2005/123665, to a marked, avoidable loss of isocyanate. According to the teaching of WO 2005/123665, it is possible in the direct cooling of the reaction mixture of the preparation of isocyanates by the gas-phase phosgenation of corresponding amines with phosgene to achieve markedly shorter cooling times with a process in which the reaction of the amines with phosgene in the gas phase takes place in a reaction zone. In order to terminate the reaction, the reaction mixture is guided through a zone in which a liquid is injected. Between the reaction zone and the zone in which the liquid is injected, the reaction mixture is guided through a zone which has a reduced flow cross-section. According to the teaching of WO 2005/123665, the constriction of the flow cross-section is chosen so that the reaction mixture, on leaving the constriction, has been markedly cooled and possesses a high flow speed, which according to the teaching of WO 2005/123665 brings about effective "secondary atomisation" of the quench liquid. According to the teaching of WO 2005/123665, both requirements can be met if the Mach number of the flow in the constriction is from 0.1 to 1.0, preferably from 0.2 to 1.0, most preferably from 0.3 to 1.0. According to the teaching of WO 2005/123665, when the reaction gas stream emerging from the cross-sectional constriction at very high speed meets the quench liquid spray produced by means of single- or two-component atomizer nozzles having a Sauter diameter $d_{23}$ of from 5 to 5000 µm, preferably from 5 to 500 µm, most preferably from 5 to 250 µm, it brings about "secondary atomisation" of the quench liquid, so that the spray has a particularly large specific surface area. According to the teaching of WO 2005/123665, the large specific surface area which can be achieved by the disclosed process, in conjunction with the high relative speed between the reaction gas and the quench liquid, causes an intensification of the exchange of material and heat between the reaction gas and the quench liquid, and the contact times required for cooling the reaction mixture are greatly reduced and the loss of valuable isocyanate product as a result of further reaction to secondary products is minimized. The necessary period of time between the entry of the reaction gas into the quench area and the time at which the reaction gas still differs by 10% from the adiabatic final temperature of the mixture of reaction gas and drops is disclosed in WO 2005/123665 as preferably from $10^{-4}$ to 10 seconds, more preferably from $5 \times 10^{-4}$ to 1.0 seconds and most preferably from 0.001 to 0.2 seconds.

A disadvantage of the process disclosed in WO 2005/123665 is that the "secondary atomisation", on which the process is based, of the quench liquid spray, which in the preferred range already consists of small droplets, involves the risk of mist formation with the consequence of a high outlay for separation of the isocyanate that has formed and the cooled reaction mixture. Another disadvantage is that, in the zone in which the cooling liquid is added, the high speed of emergence of the hot reaction mixture from the zone of reduced cross-section is to be taken into account by correspondingly increased apparatus dimensions.

SUMMARY OF THE INVENTION

The object of the present invention was to develop a process for the preparation of isocyanates by reaction of corresponding amine(s) with phosgene in the gas phase in which, once the optimum dwell time has been reached, the reaction is stopped within sufficiently short times and simple separation of the isocyanate from the remaining constituents of the reaction mixture can be achieved. Isocyanate mixtures having high isocyanate contents are obtainable and the process can be carried out in a simple, compact apparatus with minimal energy input.

It has been possible to achieve this object by guiding the isocyanate-containing reaction mixture out of the reaction chamber through a cooling stretch into which liquids are injected to terminate the reaction. Direct cooling takes place in the cooling stretch in one stage in two or more cooling zones connected in series.

DETAILED DESCRIPTION OF THE INVENTION

The present invention provides a process for the preparation of isocyanates by reaction of corresponding primary amines with phosgene, in which: a) the phosgene and the amine(s) are reacted in a reaction chamber at a temperature above the boiling point of the amine(s) within a mean contact time of from 0.05 to 15 seconds; and b) the gas mixture leaving the reaction chamber is cooled in order to condense the isocyanate that has formed. In this process, the cooling in step b) takes place by direct cooling in one stage in a cooling stretch of two or more cooling zones arranged in series. Uncondensed isocyanate is separated from the gas mixture by washing with a washing liquid.

Within the scope of the invention, "in one stage" means that the direct cooling takes place in the cooling stretch with the supply of at least one cooling liquid, only one common condensation mixture being obtained from the two or more cooling zones. A liquid collecting vessel is preferably arranged beneath the cooling stretch. The condensation mixture may be collected in this vessel. The condensation mixture can be discharged for separation of the isocyanate prepared in step a) or, preferably after cooling has taken place, part of the condensation mixture can be fed back to one or more cooling zones of the cooling stretch.

In a preferred embodiment of the process according to the invention, the reaction in step a) takes place adiabatically.

It is particularly preferred that the direct cooling in two or more cooling zones of the process of the invention use cooling liquids having the same or different compositions and having the same or different temperatures. Cooling liquids having different compositions are preferably used.

In a preferred embodiment of the process according to the invention, the direct cooling is carried out in a manner such that, in the first zone, the cooling liquid fed into the reaction mixture is a solvent-containing cooling liquid having a temperature of from 50 to 200° C. which contains (i) solvent in an amount of from 80 to 100 wt. %, based on the weight of the cooling liquid, and also (ii) the isocyanate prepared in step a) in amounts of from 20 to 0 wt. %, based on the weight of the cooling liquid. In the second and optional additional zones, the cooling liquid is the mixture obtained as the bottom product of the cooling stretch. This bottom product mixture has a temperature of from 100 to 200° C. and contains This bottom product mixture has a temperature of from 100 to 200° C. and contains solvent in amounts of from 30 to 90 wt. %, based on the weight of the cooling liquid, and further contains the isocyanate prepared in step a) in amounts of from 70 to 10 wt. %, based on the weight of the cooling liquid.

Most preferably, the amount and the solvent content of the cooling liquid used in the first cooling zone are adjusted so that, in the first cooling zone, the temperature of the isocyanate after a dwell time of from 0.001 to <0.2 second is already below a temperature of 300° C., preferably below 280° C. This is preferably achieved by using solvent contents in the cooling liquid of the first cooling zone of at least 85 wt. %, most preferably at least 90 wt. %, based on the weight of the cooling liquid, the temperature of the cooling liquid preferably being at least 50° C., most preferably at least 80° C. Very rapid cooling is achieved by the evaporation of the large amounts of solvent and the associated dissipation of the evaporation heat. The risk of formation of undesirable secondary components, which occurs especially-above 300° C., is minimized.

It is fundamental to the process of the present invention that the cooling of the reaction gases that enter the cooling stretch from the reaction chamber takes place predominantly by evaporation of solvent components of the cooling liquid (quench liquid) injected into the first cooling zone or the first cooling zones. Due to the energy required for the evaporation, it is possible, using small amounts of cooling liquid, to achieve very rapid cooling to a temperature range in a manner such that further cooling can take place in the subsequent zones without losses of yield, even at a relatively low speed. Due to the series connection of two or more cooling zones in the cooling stretch, the effect of rapid cooling of the reaction gases is achieved in the process of the present invention even when mixtures having relatively high isocyanate contents are used as the cooling liquid for the cooling zones. Because injection of the cooling liquid or cooling liquids occurs in rapid succession, adequate solvent components for the evaporation cooling that is predominantly desired are always available, even when cooling liquids having high isocyanate concentrations are used.

The process of the present invention is distinguished by high isocyanate yields with, at the same time, simple separation of the isocyanate from the cooled reaction mixture. In the preferred embodiments of this invention, particularly high isocyanate concentrations in the condensation mixture present as the bottom product of the cooling stretch are additionally obtainable by the use of different cooling liquids in the cooling zones of the single-stage cooling stretch. The use of different cooling liquids advantageously reduces the energy input required for separating the isocyanates from the condensation mixture and for processing the solvent that is used.

A particularly low energy input is achieved when: (1) in addition to the condensation mixture obtained as the bottom product of the cooling stretch containing solvent in amounts of from 30 to 90 wt. %, based on the weight of the condensation mixture, and further containing the isocyanate prepared in step a) in amounts of from 70 to 10 wt. %, based on the weight of the condensation mixture, a gas stream containing at least hydrogen chloride, phosgene and the isocyanate prepared in step a) is obtained; (2) the gas stream containing at least hydrogen chloride, phosgene and the isocyanate prepared in step a) is washed with solvent using a mixture containing solvent in amounts of from 95 to 100 wt. %, based on the weight of the mixture, and the isocyanate prepared in step a) in amounts of from 5 to 0 wt. %, based on the weight of the mixture, as the washing liquid; (3) the washing liquid obtained in the washing containing solvent in amounts of from 80 to 99.99 wt. %, based on the weight of the mixture, and the isocyanate prepared in step a) in amounts of from 20 to 0.01 wt. %, based on the weight of the mixture, is subsequently used as the cooling liquid of the first cooling zone of the cooling stretch; and (4) in the second and, optionally, the further cooling zones there is used as the cooling liquid the mixture obtained as the bottom product of the cooling stretch as a whole, containing solvent in amounts of from 30 to 90 wt. %, based on the weight of the mixture, and the isocyanate prepared in step a) in amounts of from 70 to 10 wt. %, based on the weight of the mixture.

In this embodiment, cooling of the reaction gases entering the cooling stretch from the reaction chamber takes place predominantly by evaporation of solvent components of the cooling liquid injected into the first cooling zone. Due to the energy required for the evaporation, very rapid cooling to a temperature range such that, in the subsequent zones, further cooling can take place without losses of yield even at a relatively low speed is achieved. Consequently, cooling liquids having markedly increased isocyanate contents can be used. A further advantage of this embodiment is that the washing liquids obtained in the gas washing do not have to be processed.

Any of the known processes for the preparation of isocyanates by reaction of phosgene with primary amines in the gas phase, such as are described, for example, in EP-A 0 570 799, EP-A 1 362 847, EP-A 1 526 129 or EP-A 1 555 258, may be used as step a) in the process of the present invention. It is preferred that step a) be conducted in a reaction chamber that has rotationally symmetrical geometry with a flow-through cross-sectional area that is constant or which increases in the direction of flow of the reaction mixture. A tubular reactor having a flow-through cross-sectional area that is substantially constant or increases in the direction of flow of the reaction mixture is preferred. In another preferred embodiment, the reaction chamber, preferably a tubular reactor, has sections of constant and increasing cross-sectional area in the direction of flow.

Primary amines can be used for the process according to the invention. It is preferred to use primary amines that can be converted to the gas phase without decomposition. Particularly suitable are amines, especially diamines, based on aliphatic or cycloaliphatic hydrocarbons having from 1 to 15 carbon atoms. Examples of suitable amines are 1,6-diaminohexane, 1-amino-3,3,5-trimethyl-5-aminomethylcyclohexane (IPDA) and 4,4'-diaminodicyclohexylamine. 1,6-Diaminohexane (HDA) is most preferred.

It is also possible to use aromatic amines which can preferably be converted to the gas phase without decomposition. Examples of preferred aromatic amines include toluenediamine (TDA), in particular 2,4-TDA and 2,6-TDA and mixtures thereof, diaminobenzene, naphthyldiamine (NDA) and 2,2'-, 2,4'- or 4,4'-methylenediphenyldiamine (MDA) or isomeric mixtures thereof. Toluenediamine (TDA), in particular 2,4-TDA and 2,6-TDA and mixtures thereof, are particularly preferred.

Before the process of the present invention is carried out, the starting amines are generally evaporated and heated to from 200° C. to 600° C., preferably from 201° C. to 500° C., most preferably from 250° C. to 450° C., and, optionally diluted with an inert gas such as $N_2$, He, Ar or with the vapors of an inert solvent, before being fed to the reactor. In view of the preferred use of a solvent, there are preferably used as solvents for the reaction in step a) or as cooling liquid in step b) solvents that have a low boiling point (i.e., a boiling point of <200° C.). Examples of suitable solvents include optionally halo-substituted aromatic hydrocarbons, such as chlorobenzene or o-dichlorobenzene.

The evaporation of the starting amines can be carried out in any known evaporation apparatus. Evaporation systems in which a small working content is guided with a high circulating capacity over a falling-film evaporator and, in order to minimize the thermal load on the starting amines, the evaporation process is optionally assisted by the supply of inert gas and/or vapors of an inert solvent are preferred. The amines in vapor form can still contain amounts of unevaporated droplets of amine(s) (aerosol), but the amine(s) in vapor form preferably does not contain any droplets of unevaporated amine(s). After the evaporation, the amine in vapor form, optionally diluted with inert gases or inert solvent vapors, is brought to the desired use temperature via a post-heater.

In the process of the present invention, it is advantageous to use phosgene in excess relative to amino groups. A molar ratio of phosgene to amino groups of from 1.1:1 to 20:1, preferably from 1.2:1 to 5:1, is conventionally present. The phosgene is also generally heated to temperatures of from 200° C. to 600° C. and is fed to the reactor, optionally, diluted with an inert gas such as $N_2$, He, Ar or with the vapors of an inert solvent (for example, aromatic hydrocarbons with or without halogen substitution, such as chlorobenzene or o-dichlorobenzene).

The process of the present invention is generally carried out by introducing separately heated reactants into at least one reactor, mixing and reacting the reactants for a suitable reaction time. The reaction is carried out adiabatically in a preferred embodiment. In the process of the present invention, the necessary dwell time for the reaction of the amine groups with the phosgene to form isocyanate is preferably from 0.05 to 15 seconds, depending on the type of amine used, the reaction temperature, or in the case of the adiabatic reaction procedure the starting temperature and the adiabatic temperature rise in the reactor, the molar ratio of amine to phosgene and any dilution of the reactants with inert gases.

Once the amine used in step a) has been phosgenated with phosgene to form the desired isocyanate(s), the gas mixture leaving the reaction chamber is effectively cooled in step b) in order to avoid the formation of undesirable secondary products by thermal decomposition of the isocyanate or by a further reaction. To this end, the gas mixture leaving the reaction chamber, which preferably comprises at least one isocyanate, phosgene and hydrogen chloride, is directly cooled with the supply of cooling liquid in the cooling stretch, which has two or more cooling zones arranged in series in the direction of flow.

In a preferred embodiment, the cooling stretch is immediately adjacent to the reaction chamber. In a further preferred embodiment, the geometry of the flow-through cross-sectional area of the outlet from the reaction chamber corresponds to the geometry of the flow-through cross-sectional area of the inlet into the cooling stretch.

In order to carry out effective cooling, there is preferably used a cooling stretch which has rotationally symmetrical geometry with a cross-sectional area that is constant or that increases in the direction of flow of the gas mixture. A rotationally symmetrical cooling stretch with a flow-through cross-sectional area that is substantially constant or increases in the direction of flow of the gas mixture is preferably used. In a further preferred embodiment, the cooling stretch, which is preferably rotationally symmetrical, has sections of constant and increasing cross-sectional area in the direction of flow.

The forms of the cooling stretch that are suitable for the present invention with a cascade-like and/or continuous enlargement of the flow-through cross-sectional area in the direction of flow of the gas mixture can be selected to adjust the speed of the gas mixture along the axis of the cooling stretch.

The constructive form of the two or more cooling zones in the cooling stretch can be in accordance with any of the forms known to be suitable from the prior art. In a preferred embodiment, the cooling stretch is constructed in accordance with the teaching of EP-A 1 403 248. According to the teaching of EP-A 1 403 248, the cooling liquid is injected in the cooling zone by means of at least two spray nozzles which are arranged at the entrance to the cooling zone at equal intervals along the periphery of the cooling zone. The spray nozzles can be single nozzles. Preferably, however, nozzle heads each having at least two single nozzles are used, single-component nozzles preferably being chosen.

The nozzles used in the process of the present invention preferably produce liquid droplets having a Sauter diameter $d_{50}$ of preferably from 100 to 5000 µm, more preferably from 100 to 2500 µm and most preferably from 100 to 1000 µm. The Sauter diameter $d_{50}$ describes, to a constant factor, the ratio of the drop volume to the drop surface area (K. Schwister: Taschenbuch der Verfahrenstechnik, Fachbuchverlag Leipzig, Carl Hanser Verlag 2003).

The spray nozzles are preferably arranged independently of one another in a manner such that the direction of flow of the cooling liquid in each case has an angle of from 0° to 50°, preferably from 200 to 35°, relative to the direction of flow of the gas mixture. The direction of flow of the gas mixture runs substantially along the axis of the cooling zones, which are preferably rotationally symmetrical in form. In the case of a preferred vertical arrangement of the cooling stretch, the reaction gas emerging from the reaction zone flows from top to bottom through the cooling stretch and its cooling zones. The direction of flow of the cooling liquid along the axis of the respective spray nozzles runs analogously. The aperture angle of the spray nozzles, independently of one another, is preferably from 20° to 90°, most preferably from 30° to 60°. When choosing the inlet angle of the cooling liquids, and also when choosing the aperture angle of the spray nozzles, account is taken of the fact that the cooling liquid is sprayed into the gas stream in a manner such that the hot reaction mixture does not come into contact with the relatively cold surfaces of the cooling zones or of the nozzles or their pipes. Only when the gas mixture has been cooled to the stable temperature range for the particular isocyanate in question does it come into contact with the relatively cold walls of the cooling zones or other structural components.

Suitable cooling liquids for use in the cooling zones of the cooling stretch are organic solvents or a mixture of different solvents which do not react with the isocyanate that has formed, or a solution of the isocyanates that have formed in such solvents. In a preferred embodiment, the solvent or solvent mixture that has optionally been used for diluting the reaction components in step a) is used in the cooling stretch. In a particularly preferred embodiment, the solvent or solvent mixture that is optionally used in step a) for diluting the reaction components and likewise for washing the waste gas stream produced in the cooling step is used in the cooling stretch. Examples of suitable solvents include toluene, chlorotoluene, xylene, preferably, monochlorobenzene and o-dichlorobenzene.

In a particularly preferred embodiment, the cooling solution is a liquid solution of the isocyanate that has formed in a suitable solvent, preferably predominantly the mixture obtained as the bottom product of the cooling stretch and containing solvents in amounts of from 30 to 90 wt. %, based on the weight of the mixture, and the isocyanate prepared in step a) in amounts of from 70 to 10 wt. %, based on the weight of the mixture. It is also particularly preferred to use as the cooling liquid the mixture obtained from washing the waste gas stream produced in the cooling step containing solvents in amounts of from 80 to 99.99 wt. %, based on the weight of the mixture, and isocyanate prepared in step a) in amounts of from 20 to 0.01 wt. %, based on the weight of the mixture. It is also possible to use mixtures of the two described cooling liquids.

During operation of the cooling stretch, the use of the cooling liquids injected into the separate cooling zones is chosen so that very effective cooling of the reaction mixture that enters the cooling stretch in gas form is achieved and the temperature of the cooling zone is preferably above the decomposition temperature of the carbamic acid chloride corresponding to the isocyanate. The temperature control in the second and any subsequent cooling zones is achieved by the condensation or dissolution in solvent of both the isocyanate and, preferably, the solvent optionally used as diluent in the amine vapor stream and/or phosgene stream or converted to the gas phase during the evaporation cooling and the flow of the condensed or dissolved isocyanate into the collecting vessel provided downstream of the cooling stretch, while excess phosgene, hydrogen chloride and inert gas optionally used as diluent flow through the cooling stretch and to the collecting vessel provided downstream.

The use of the cooling liquids injected into the separate cooling zones is preferably carried out in a manner such that the temperature of the reaction mixture, starting preferably at from 250° C. to 450° C., is lowered by 150° C. to 350° C., preferably by 100° C. to 300° C., and the desired temperature drop takes place over the cooling stretch preferably in from 0.1 to 10 seconds, more preferably in from 0.1 to 3 seconds and most preferably in from 0.1 to 1 second. The temperature of the cooling liquids injected into the cooling zones is preferably from 50° C. to 200° C., most preferably from 80° C. to 180° C. In particular, in a preferred embodiment, cooling liquids having different temperatures are used for the individual cooling zones of the cooling stretch.

After passing through the cooling stretch, the liquid/gas mixture produced in the cooling stretch is fed to a collecting vessel provided downstream of the cooling stretch. The collecting vessel is preferably immediately adjacent to the cooling stretch, which is preferably arranged vertically. The collecting vessel separates the gas and the liquid. As a result of the phase separation, a liquid mixture (condensation mixture) containing solvent in amounts of from 30 to 90 wt. %, based on the weight of the mixture, and the isocyanate prepared in step a) in amounts of from 70 to 10 wt. %, based on the weight of the mixture, and a gas stream containing at least hydrogen chloride, phosgene and the isocyanate prepared in step a) are obtained.

The liquid mixture (condensation mixture) obtained in the collecting vessel can be discharged for separation of the isocyanate prepared in step a) or, preferably after cooling has taken place, and a portion thereof can be fed back to one or more cooling zones of the cooling stretch.

Separation of the isocyanate prepared in step a) from the discharged liquid mixture (condensation mixture) can be carried out by any methods known to those skilled in the art. Distillation is the preferred separation method.

In a preferred embodiment, cooling of the liquid mixture (condensation mixture) used as cooling liquid in one or more zones of the cooling stretch is carried out by indirect cooling. In a particularly preferred form, the heat removed from the liquid mixture by the indirect cooling is used to produce steam. Any of the methods for producing low-pressure steam known to those skilled in the art can be used. In a further preferred form, the heat removed from the liquid mixture by the indirect cooling can be used for heating and/or evaporating process streams.

The gas stream obtained in the collecting vessel and containing at least hydrogen chloride, phosgene and the isocyanate prepared in step a) is preferably removed from the collecting vessel and fed to a washing column, in which it is largely freed of its isocyanate components. Any of the methods known to those skilled in the art are suitable for use in the washing column, but washing is preferably carried out counter-currently. In a preferred embodiment of the invention, the mixture obtained as the wash phase in the gas washing and containing solvent in amounts of from 80 to 99.99 wt. %, based on the weight of the mixture, and the isocyanate prepared in step a) in amounts of from 20 to 0.01 wt. %, based on the weight of the mixture, is used in the cooling step as the cooling liquid of the first cooling zone of the cooling stretch.

The residual gas obtained downstream of the washing column and containing phosgene, hydrogen chloride and residues of solvent used may subsequently be freed of excess phosgene in any manner known to those skilled in the art. This can be done by means of a cooling trap, absorption in an inert solvent maintained at a temperature of from −20° C. to 8° C. (preferably in chlorobenzene or dichlorobenzene), or by adsorption and hydrolysis on activated carbon. The hydrogen chloride gas passing through the phosgene separation stage can be used for further chemical reactions, be processed further to form hydrochloric acid, or be recycled in order to recover the chlorine necessary for the phosgene synthesis.

The process of the present invention is described in greater detail hereinbelow by means of Examples which illustrate preferred embodiments of the invention.

EXAMPLES

Example 1

Phosgenation of an Aromatic Diisocyanate (TDI)

20.5 kmol/h of a mixture composed of 2,4- and 2,6-toluenediamine in a weight ratio of 80% to 20% were evaporated together with 500 kg/h of nitrogen at a temperature of 320° C. and fed in gas form to the reactor. In parallel, 182 kmol/h of gaseous phosgene were heated to 360° C. together with 1000 kg/h of ortho-dichlorobenzene and likewise fed to the reactor. The streams were mixed and entered the reaction chamber. The reaction was carried out under adiabatic conditions. The gas mixture that left the reaction chamber after 5.5 seconds at a temperature of 405° C. was cooled in one stage in a cooling stretch having two cooling zones. A cooling liquid containing 97 wt. % ortho-dichlorobenzene and having a temperature of 150° C. was used in the first cooling zone. A cooling liquid containing 74 wt. % ortho-dichlorobenzene and having a temperature of 160° C. was used in the second cooling zone. In the first cooling zone, the product temperature fell below 275° C. within <0.2 second. The temperature difference between the inlet into the cooling stretch and the outlet from the cooling stretch was >200° C. for a mean dwell time of 1 second in the cooling stretch. The condensation mixture from the cooling stretch was collected in a collecting vessel and then worked up by distillation according to known methods to form the end product. The region of the cooling zones exhibited no or only slight caking above and beneath the quench nozzles even after an operating time of months. The gas outlet region of the separator did not exhibit any contamination.

The gas stream leaving the collecting vessel was fed to a washing column and was washed counter-currently therein with ortho-dichlorobenzene. The wash liquid obtained was used as the cooling liquid in the first cooling zone of the cooling stretch.

Example 2

Phosgenation of an Aliphatic Diisocyanate (HDI)

25.8 kmol/h of 1,6-diaminohexane were evaporated together with 30 kg/h of nitrogen and fed in gas form, superheated to a temperature of 300° C., to a tubular reactor. At the same time, 110 kmol/h of gaseous phosgene were heated in parallel to 300° C. and likewise fed to the tubular reactor. The streams were mixed within a mixing time of 0.04 second and entered the reaction chamber. The mixing zone and the reaction chamber were heat insulated so that the reaction was carried out under adiabatic conditions. A final temperature of 440° C. was measured at the outlet of the reaction chamber by means of a surface thermometer. The gas mixture that left the reaction chamber after 0.23 second was cooled in one stage in a cooling stretch having two cooling zones. This was carried out by cooling the gas mixture in a first cooling zone in the course of 0.2 second to a product temperature <270° C. by injection of a cooling liquid containing 98 wt. % monochlorobenzene and having a temperature of 80° C. and in a second cooling zone by injection of a cooling liquid containing 60 wt. % monochlorobenzene and having a temperature of 130° C. at a mean dwell time of 1.6 seconds. The condensable constituents were dissolved in the cooling liquid, and the amount of monochlorobenzene required for cooling was evaporated off. The liquid/gas mixture was introduced into a separator. The temperature of the concentrated diisocyanate solution collected in the separator was 130° C., the gas leaving the separator had a temperature of 133° C.

The region of the cooling zones exhibited no or only slight caking above and below the quench nozzles even after an operating time of months. The gas outlet region of the separator did not exhibit any contamination.

The gas stream leaving the separator was fed to a washing column, where it was washed counter-currently with monochlorobenzene. The wash liquid obtained was used as the cooling liquid in the first cooling zone of the cooling stretch.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an isocyanate by reacting a primary amine with phosgene comprising:
   a) reacting the phosgene and the primary amine in a reaction chamber at a temperature greater than the amine's boiling point within a mean contact time of from 0.05 to 15 seconds to form a gaseous, isocyanate-containing mixture,
   b) cooling the gaseous isocyanate-containing mixture leaving the reaction chamber to condense the isocyanate present therein by direct cooling in one stage in a cooling stretch in two or more cooling zones arranged in series, and
   c) washing the gaseous mixture from step b) with a washing liquid to separate any uncondensed isocyanate from the gaseous mixture.

2. The process of claim 1 in which that the reaction in step a) is conducted adiabatically.

3. The process of claim 1 in which two or more cooling liquids having different compositions are used in step b).

4. The process of claim 3 in which the cooling liquids have different temperatures.

5. The process of claim 1 in which the cooling step b) comprises:
   (i) feeding into the first cooling zone a first solvent-containing cooling liquid having a temperature of from 50 to 200° C., a solvent content of from 80 to 100 wt. %, based on total weight of the cooling liquid, and up to 20 wt. % of the isocyanate produced in step a), based on total weight of the cooling liquid, and
   (ii) feeding into the second and any subsequent cooling zones a second solvent-containing cooling liquid having a solvent content of from 30 to 90 wt. %, based on total weight of the cooling liquid, and from 10 to 70 wt. % of the isocyanate produced in step a), based on total weight of the cooling liquid, which second solvent-containing cooling mixture is obtained as a bottom product of the cooling stretch.

6. The process of claim 5 in which the amount and the solvent content of the first solvent-containing cooling liquid are such that, in the first cooling zone, the temperature of the isocyanate after a dwell time of from 0.001 to <0.2 second is below 300° C.

7. The process of claim 5 in which a gas stream comprising hydrogen chloride, phosgene and the isocyanate is obtained.

8. The process of claim 7 in which the gas stream comprising hydrogen chloride, phosgene and the isocyanate is washed with a washing mixture comprising from 95 to 100 wt. % solvent, based on total weight of the washing mixture and up to 5 wt. % of the isocyanate.

9. The process of claim 8 in which washing liquid comprising from 80 to 99.99 wt. % solvent, based on total weight of the washing liquid, and from 0.01 to 20 wt. % of the isocyanate, based on total weight of the washing liquid, is subsequently used as the cooling liquid of the first cooling zone of the cooling stretch.

10. The process of claims 1 in which the cooling stretch has rotationally symmetrical geometry with a cross-sectional area that is constant or increases in the direction of flow of the gas mixture.

11. The process of claim 1 in which the cooling stretch has rotationally symmetrical geometry with a constant and increasing flow-through cross-sectional area arranged in succession in the direction of flow of the gas mixture.

* * * * *